United States Patent [19]

Molinari

[11] Patent Number: 4,639,449

[45] Date of Patent: Jan. 27, 1987

[54] MORPHOLINE CONTAINING PROPIONYLANILIDES AND PHARMACEUTICAL COMPOSITIONS

[75] Inventor: Egidio Molinari, Longone al Segrino, Italy

[73] Assignee: Erregierre Industria Chimica Spa, San Paolo d'Argon (BG), Italy

[21] Appl. No.: 854,789

[22] Filed: Apr. 23, 1986

[30] Foreign Application Priority Data

May 15, 1985 [IT] Italy .............................. 20726 A/85

[51] Int. Cl.$^4$ .................. A61K 31/535; C07D 295/18
[52] U.S. Cl. ..................................... 514/234; 544/165
[58] Field of Search ......................... 544/165; 514/234

[56] References Cited

U.S. PATENT DOCUMENTS 3,661,903  5/1972  Kruger et al. ...................... 544/165

Primary Examiner—Robert W. Ramsuer
Attorney, Agent, or Firm—Stevens, Davis, Miller & Mosher

[57] ABSTRACT

Propionylanilides, and relative salts of addition, having the following general formula:

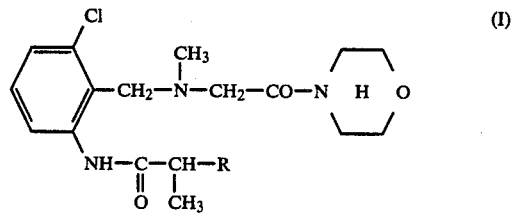

The new compounds are useful in the treatment of morbid cold-induced forms.

2 Claims, No Drawings

MORPHOLINE CONTAINING PROPIONYLANILIDES AND PHARMACEUTICAL COMPOSITIONS

This invention relates to new propionylanilides, and to the relative salts of addition, which possess useful pharmacological properties. The invention also relates to the process for preparing said propionylanilides and the relative salts of addition.

More particularly, the invention relates to propionylanilides and to the relative salts of addition with physiologically compatible inorganic or organic acids, have the following general formula:

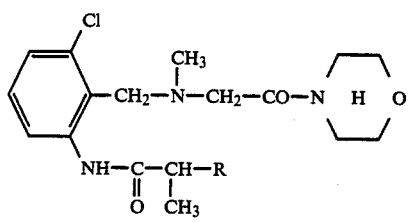

in which R is a radical chosen from the group consisting of 4-isobutylphenyl, 3-benzoylphenyl, 6-methoxy-2-naphthyl and 2-fluoro-4-diphenyl.

Compounds of formula (I) all possess centres of asymmetry, and can therefore be prepared in both racemic and optically active forms, these forms in all cases falling within the scope of the present invention.

Aryl-propionic acids of general formula:

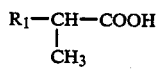

in which $R_1$ represents an aryl group and in particular has the same meaning as R, are known to possess anti-inflammatory, analgesic and antipyretic activity.

These acids are used, inter alia, in the treatment of those morbid forms known as cold-induced illnesses and characterised generally by inflammation of the respiratory passages accompanied by coughing, this symptom increasing the patient's suffering.

The acids of formula (II) do not however exhibit antitussive action, and this constitutes a disadvantage in the treatment of cold-induced forms.

We have now discovered that this disadvantage can be overcome by the propionylanilides according to the present invention, which besides exhibiting anti-inflammatory, analgesic and/or antipyretic activity also exhibit effective antitussive action which makes them particularly suitable for the treatment of cold-induced morbid forms.

The propionylanilides of formula (I) according to the present invention are prepared by reacting a reactive derivative of the acids of formula:

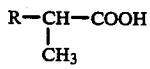

with an aniline derivative of formula:

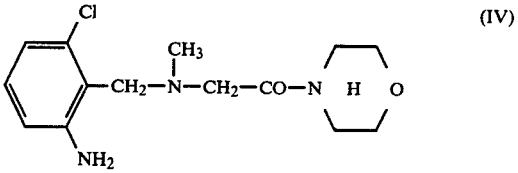

in a reaction medium consisting of an inert organic solvent.

The characteristics of the process for preparing the compounds according to the invention and their pharmacological properties will be more apparent from the detailed description given hereinafter.

According to a preferred preparation process, a halide, advantageously the chloride, of the acid of formula (III) is reacted with an analine derivative of formula (IV). The reaction medium consists of an inert organic solvent such as carbon tetrachloride or dichloroethane, under substantially anhydrous conditions. The reaction is preferably conducted in the presence of acid acceptors such as aliphatic, aromatic and/or heterocyclic tertiary amines, for example trimethylamine, triethylamine and pyridine, which can also form the reaction medium.

The ratio of the halide of the acid of formula (III) to the aniline derivative of formula (IV) is substantially equimolar and preferably between 1:0.9 and 1:1.1. The tertiary amine is preferably used in excess over the acid chloride. The halide of the acid of formula (III) is added to the solution of the aniline derivative of formula (IV) in an organic solvent, under agitation and at low feed rate so as not to exceed a temperature of 50° C., the temperature preferably being maintained between 5° C. and 30° C.

The reaction mixture is reacted with an aqueous solution of sulphuric acid containing between 50 and 200 g/l of $H_2SO_4$, and the sulphuric solution is alkalified with a 30 weight% NaOH solution which is added slowly so as not to exceed a temperature of 25° C.

The product which separates is extracted by treatment with dichloroethane, and the organic phase is washed with water until neutral and is dried under vacuum.

The residue is dissolved in ligroin and the solution is filtered and preferably treated with a physiologically compatible inorganic or organic acid to separate the product in the form of a salt of addition, for example as the hydrochloride, which is a white solid generally poorly solublein water, in ether and in other apolar solvents, but soluble in dimethylformamide.

As stated heretofore, the compounds according to the present invention exhibit anti-inflammatory, analgesic and/or antipyretic activity, in addition to antitussive activity.

Pharmacological tests were carried out on the compounds of formula (I) in order to examine the following characteristics:

anti-inflammatory activity;
analgesic activity;
antipyretic activity;
antitussive activity;
acute toxicity.

The anti-inflammatory activity was determined by the carrageen-induced edema test in the rat, in accordance with Winter et al. (1962).

Three groups of animals each consisting of 10 animals were treated as follows:

Group 1: controls;
Group 2: treatment with 10 mg/kg of compound by oral administration;
Group 3: treatment with 50 mg/kg of compound by oral administration.

All the compounds examined displayed good antiedematous activity both at the dose of 10 mg/kg with inhibition of 50-55%, and at the dose of 50 mg/kg with inhibition of 60-65%.

The analgesic activity was determined by the hot plate test on the rat in accordance with Eddy and Leinbach (1953), using the same administration scheme as heretofore described.

With both the used doses, the time of reaction to heat was about 30% greater than that found for the controls.

The antipyretic activity was determined by the test of Glenn et al., (1973) carried out on the rat at a dose of 3.7 mg/kg by oral administration.

The product under examination was administered on temperature rise, and the temperature changes recorded 2 hours and 5 hours after this administration demonstrated the high activity of the products according to the invention, which tend to restore temperature to its basic value within 2 hours, whereas there is on the average a slight temperature rise after 5 hours, as shown by the following table:

| Time 0 Administration of pyrogenic agent | Time 1 Administration of product | After 2 hours | After 5 hours |
| --- | --- | --- | --- |
| 35.6 ± 0.14° C. | 36.6 ± 0.21° C. | 35.1 ± 0.09° C. | 36.0 ± 0.13° C. |

The antitussive activity was determined by the test involving experimental cough induction in the rat by citric acid in accordance with Engelhorm and Puschman (1963).

Three groups of animals each consisting of 10 animals were treated as follows:
Group 1: controls;
Group 2: treatment with 35 mg/kg of compound by oral administration;
Group 3: treatment with 70 mg/kg of compound by oral administration.

The average percentage change in the number of coughs recorded 30 minutes after treatment was −40% at 35 mg/kg and −48% at 70 mg/kg as mean values.

With regard to acute toxicity, tests carried out on the new compounds under examination showed no deceased animals even at the maximum dose used (2000 mg/kg by oral administration), after keeping the animals under observation for 15 days.

The following examples are given as non-limiting illustration of the process for preparing the products according to the invention.

EXAMPLE 1

A solution of 140 g (0.0470 moles) of 3'-chloro-β-[N-methyl-N-(Morpholinocarbonyl-methyl)]aniline (compound of formula IV) in 1300 ml of carbon tetrachloride and containing 51 g of triethylamine is treated dropwise with 112.5 g (0.501 moles) of the chloride of 2-(4-isobutyl-phenyl)propionic acid.

The addition is carried out slowly so that the temperature does not exceed 20° C. The reaction mixture is kept at 20° C. for one hour under agitation, and is then extracted repeatedly with a sulphuric acid solution containing 100 g/l of $H_2SO_4$.

The sulphuric solution is alkalified with 30 weight% sodium hydroxide solution without exceeding 20°-25° C., and the product which separates is extracted with dichloroethane. The organic phase is washed with water until neutral, dried over anhydrous sodium sulphate and evaporated to dryness under vacuum at ambient temperature.

The residue is taken up in ligroin, the solution if filtered through activated carbon and is then treated with hydrochloric acid gas.

The 4-isobutylphenyl-propionylanilide hydrochloride precipitates as a crystalline white solid, and is filtered off, washed with ligroin and dried under vacuum at 50° C.

| | C % | H % | Cl % | N % |
| --- | --- | --- | --- | --- |
| calculated for $C_{27}H_{37}Cl_2N_3O_3$ | 62.064 | 7.137 | 13.57 | 8.042 |
| found | 61.97 | 7.21 | 13.68 | 8.10 |

EXAMPLE 2

Example 1 was repeated using the same aniline derivative but the following acid chlorides:
2-(3-benzoylphenyl)propionic;
d-2-6-methoxy-2-naphthyl)propionic;
2-(2-fluoro-4-diphenyl)propionic.

The following corresponding propionylanilides were obtained:
3-benzoylphenyl-propionylanilide;
d-α-6-methoxy-2-naphthyl-propionylanilide;
2-fluoro-4-diphenyl-propionylanilide;
which on analysis gave the following results:

| 3-benzoylphenyl-propionylanilide | | | | |
| --- | --- | --- | --- | --- |
| | C % | H % | Cl % | N % |
| calculated for $C_{30}H_{33}Cl_2N_3O_4$ | 64.981 | 5.998 | 12.787 | 7.577 |
| found | 65.01 | 5.97 | 12.98 | 7.42 |

| d-α-6-methoxy-2-naphthyl-propionylanilide | | | |
| --- | --- | --- | --- |
| | C % | H % | Cl % |
| N % calculated for $C_{28}H_{33}Cl_2N_3O_4$ | 61.539 | 6.086 | 12.974 | 7.689 |
| found | 61.63 | 6.11 | 13.1 | 7.48 |

| 2-fluoro-4-diphenyl-propionylanilide | | | |
| --- | --- | --- | --- |
| | C % | H % | N % |
| calculated for $C_{29}H_{32}Cl_2N_3O_3F$ | 62.142 | 5.764 | 7.476 |
| found | 61.98 | 5.81 | 7.61 |

I claim:
1. Propionylanilides, and relative salts of addition, of formula:

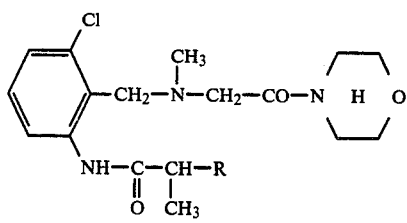 (I)
in which R is chosen from the group consisting of 4-isobutyl-phenyl, 3-benzoylphenyl, 6-methoxy-2-naphthyl and 2-fluoro-4-diphenyl.
2. Pharmaceutical compositions containing as active principle at least one propionylanilide claimed in claim 1, together with pharmacologically acceptable dispersants and/or diluents.
* * * * *